(12) United States Patent
Toriumi et al.

(10) Patent No.: US 6,214,009 B1
(45) Date of Patent: Apr. 10, 2001

(54) RHINOPLASTY BUR

(75) Inventors: Dean Toriumi, Riverside, IL (US); Gary Peters, Jacksonville, FL (US)

(73) Assignee: Xomed Surgical Products, Inc., Jacksonville, FL (US)

( * ) Notice: Subject to any disclaimer, the term of this patent is extended or adjusted under 35 U.S.C. 154(b) by 0 days.

(21) Appl. No.: 09/392,798

(22) Filed: Sep. 9, 1999

Related U.S. Application Data

(60) Provisional application No. 60/099,561, filed on Sep. 9, 1998.

(51) Int. Cl.[7] ............................. A61B 17/00; A61B 17/32
(52) U.S. Cl. .................................................. 606/80
(58) Field of Search ................... 606/80, 83, 84, 606/170, 172, 180

(56) References Cited

U.S. PATENT DOCUMENTS

| | | | |
|---|---|---|---|
| 1,493,240 | * 5/1924 | Bohn | 606/80 |
| 2,429,356 | * 10/1947 | Hicks | 606/172 |
| 3,308,828 | * 3/1967 | Pippin | 606/80 |
| 3,732,858 | * 5/1973 | Banko | 606/170 |
| 4,646,738 | 3/1987 | Trott. | |
| 5,383,884 | * 1/1995 | Summers | 606/170 |
| 5,437,630 | * 8/1995 | Daniel et al. | 606/170 |
| 5,456,689 | * 10/1995 | Kresch et al. | 606/170 |
| 5,478,093 | * 12/1995 | Eibl et al. | 279/51 |
| 5,755,718 | * 5/1998 | Sklar | 606/80 |
| 5,807,401 | * 9/1998 | Grieshaber et al. | 606/170 |

* cited by examiner

*Primary Examiner*—John J. Wilson
*Assistant Examiner*—Eduando C. Robert

(57) ABSTRACT

A rhinoplasty bur for use with a powered handpiece includes an outer tubular member configured to form a pocket for receiving a bur and for protecting the bur during operation. In one embodiment, the pocket has an end wall extending from a bottom wall of the pocket to form a distal lip providing protection for distal movement of the bur. In another embodiment, with or without the lip, the pocket is formed with opposed, curved wings extending laterally from longitudinal edges of the pocket for protection and stabilization of the bur during operation.

6 Claims, 4 Drawing Sheets

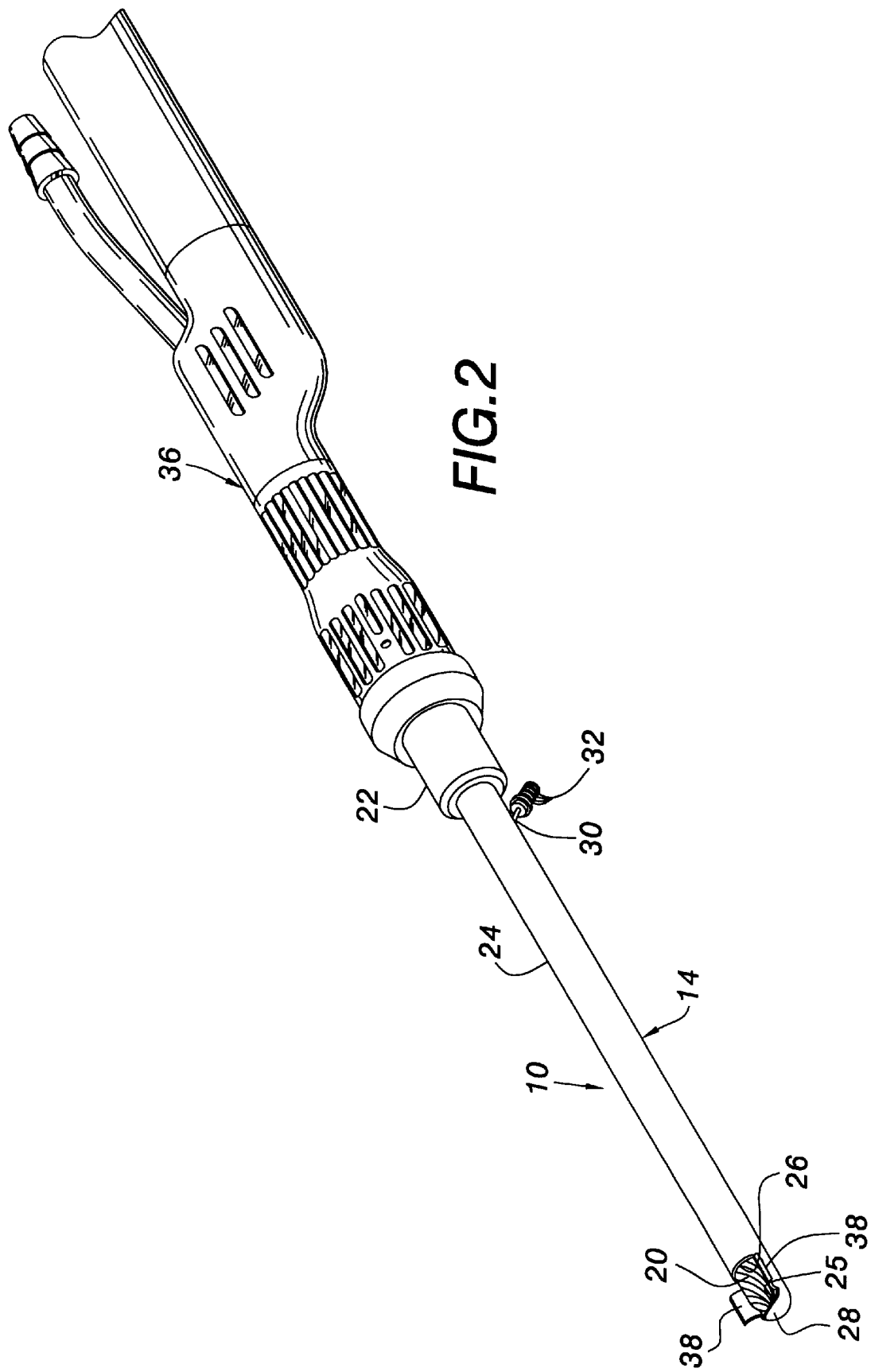

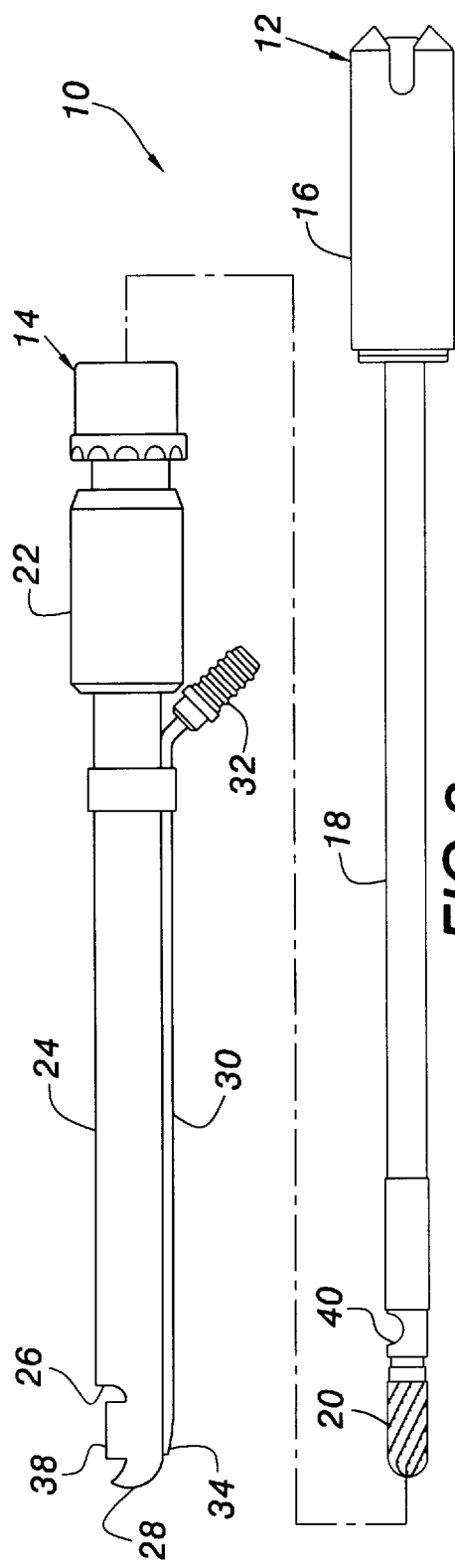
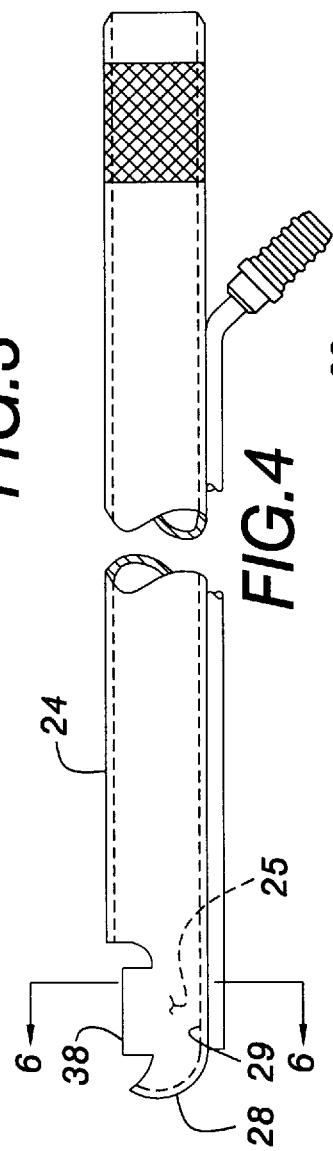
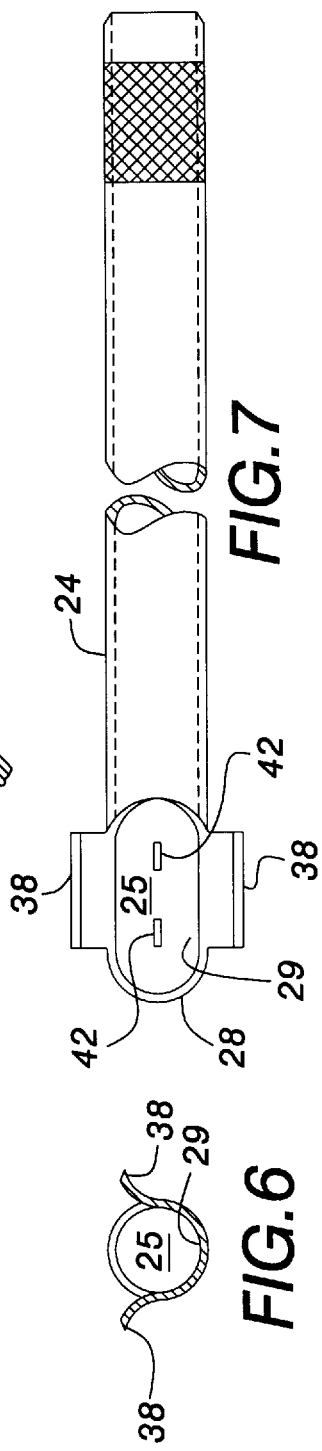

RHINOPLASTY BUR

CROSS-REFERENCE TO RELATED PATENT APPLICATIONS

This application claims priority to U.S. provisional application Serial No. 60/099,561, filed Sep. 9, 1998, the entire disclosure of which is incorporated herein by reference.

BACKGROUND AND SUMMARY OF THE INVENTION

The present invention pertains to rhinoplasty burs and, more particularly, to rhinoplasty burs adapted to be driven by powered handpieces for protected and delicate removal and shaping of bone during rhinoplasty procedures.

Rhinoplasty procedures are conventionally performed using manual osteotomes. It would be desirable to use powered burs in such procedures; however, when powered burs are used, there is a great need to protect against inadvertent tissue contact and damage and to provide bur stability during operation.

Accordingly, it is an object of the present invention to configure a rhinoplasty bur to protect soft tissues in the anterior and lateral areas and to provide integral suction and irrigation aid for evacuation of cut tissue or debris.

Another object of the present invention is to permit rhinoplasty surgeons to sculpt the bony dorsum with a high degree of finesse and control, to achieve a more reproducible dorsal hump removal, to allow spot burring to correct localized irregularities and to reduce soft tissue trauma compared to use of a rasp.

The present invention is generally characterized in a rhinoplasty bur having an outer tubular member configured with an end wall forming a lip to hood or shield the bur. The rhinoplasty bur can also be provided with opposed, laterally extending, curved distal wings for stabilization during operation.

These and other objects and advantages can be accomplished individually or in combination by use of a powered shaver having a blade assembly in accordance with the present invention.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

BRIEF DESCRIPTION OF THE DRAWINGS

FIG. 2 is a perspective view of a modification of a rhinoplasty bur according to the present invention attached to a powered handpiece.

FIG. 3 is an exploded side view of the rhinoplasty bur shown in FIG. 2.

FIG. 4 is an enlarged view of the outer tube for the rhinoplasty bur shown in FIG. 2.

FIG. 5 is a front view of the outer tube shown in FIG. 4.

FIG. 6 is a sectional view taken through line 6—6 in FIG. 4.

FIG. 7 is a top view of the outer tube shown in FIG. 4.

DESCRIPTION OF THE PREFERRED EMBODIMENT

Figure 1:
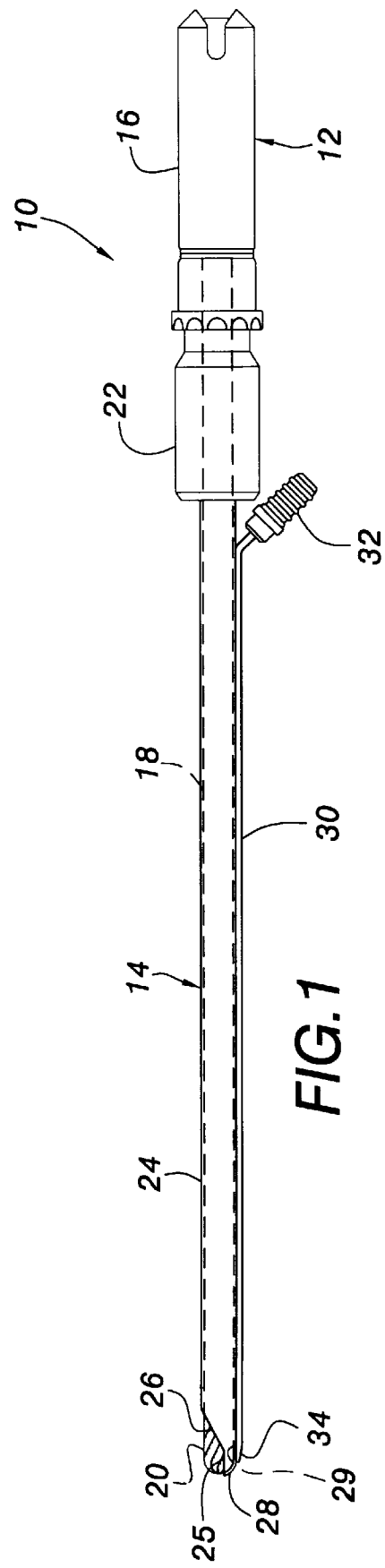
FIG. 1 is a side view of a rhinoplasty bur according to the present invention.

A rhinoplasty bur 10 according to the present invention for use with a powered handpiece is illustrated in FIG. 1 and includes an inner bur assembly 12 rotatably received within an outer tubular member 14. Inner assembly 12 includes a hub 16, a tubular drive shaft 18 extending distally from the hub, and a cutting tip 20 in the form of a bur at the distal end of the tubular drive shaft. Outer member 14 includes a hub 22 and an outer tube 24 extending distally from the hub. A pocket 25 is formed at the distal end of outer tube 24 to permit the bur to cut or abrade bodily tissue, and includes an upper opening extending only part way across the distal end of the tubular member to define a lip or end wall 28 extending from a bottom wall 29 of the pocket and providing distal protection for the bur during rhinoplasty procedures. An irrigation or injector tube 30 extends along an exterior of outer tubular member 24 from a port or coupling 32 at a proximal end to a closed distal end 34 with an aperture (not shown) formed on a side of the tube 30 in communication with an inlet (not shown) in the outer tube adjacent the cutting tip to deliver irrigating fluid to the cutting tip.

Figure 8:
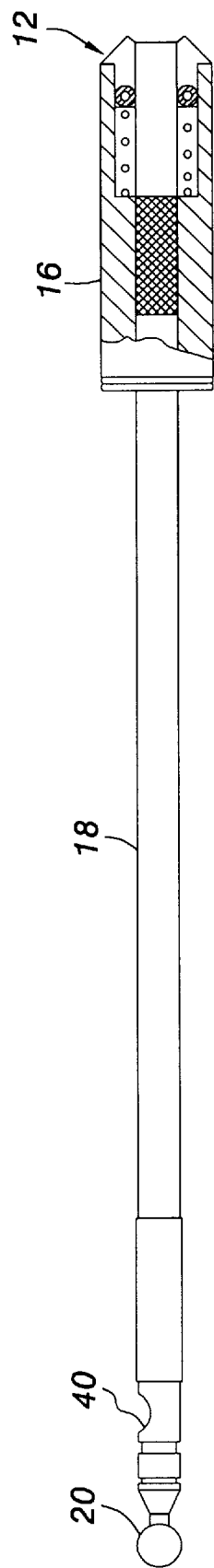
FIG. 8 is a side view of another inner assembly for a rhinoplasty bur according to the present invention.
Figure 9:
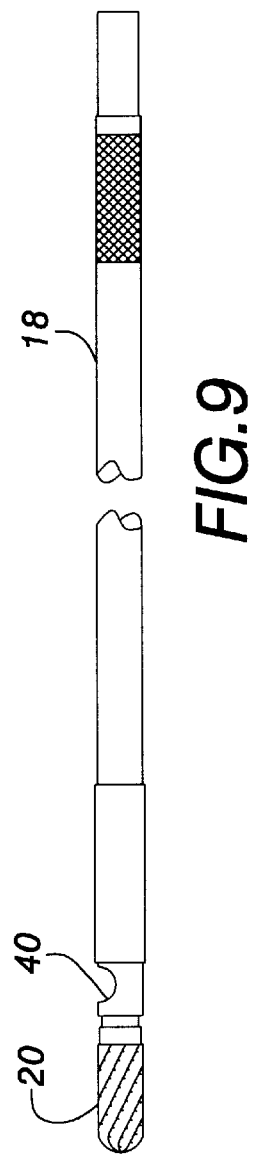
FIGS. 9 and 10 are a side view and a top view, respectively, of another inner assembly for a rhinoplasty bur according to the present invention.
Figure 10:
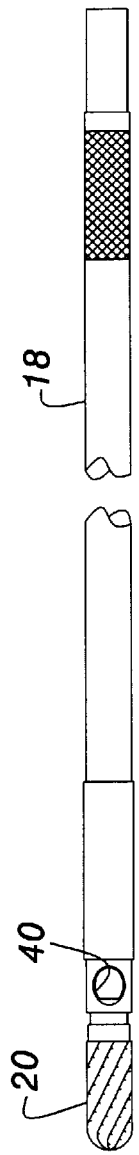

A modification of a rhinoplasty bur 10 according to the present invention is shown attached to a powered handpiece 36 in FIG. 2. Handpiece 36 is shown as the STRAIGHTSHOT®, marketed by Xomed Surgical Products, Inc. and shown in U.S. Pat. No. 5,916,231 to Bays, the disclosure of which is incorporated herein by reference; however, the rhinoplasty bur according to the present invention can be configured for use with any conventional powered handpiece. As best seen in FIG. 3, the modified rhinoplasty bur 10 includes inner and outer assemblies 12 and 14 similar to those shown in FIG. 1. Inner assembly 12 includes a hub 16 and a drive shaft 18 extending distally from the hub to a cutting tip 20 in the form of a cylindrical bur with a hemispherical end. A detailed cross-sectional view of an exemplary hub 16 is shown in FIG. 8 along with an alternative cutting tip 20 in the form of a spherical bur. While cylindrical and spherical (round) bur configurations are shown, it will be appreciated that other configurations can be used including, but not limited to, hemispherical, ellipsoidal and pear-shaped bur configurations. FIGS. 8, 9 and 10 further illustrate a suction inlet 40 which can be formed adjacent the cutting tip at the distal end of inner assembly 12 to communicate with a lumen defined by the tubular drive shaft to allow simultaneous tissue evacuation and bur cleaning.

Outer tubular member 14 of the modified bur includes a hub 22 and an outer tube 24 extending distally from the hub to pocket 25 with the opening or window 26 extending part way across the diameter of the tube to define lip or end wall 28 providing distal protection for the bur during rhinoplasty procedures. In addition, as best seen in FIGS. 4–7, curved wings or flaps 38 extend laterally outward from opposed, longitudinal edges of opening 26 at the distal end of outer tube 24 to provide extreme radial protection beyond the cutting area while burring dorsal bone during either open or closed rhinoplasty procedures. Wings 38 also provide a means for the surgeon to stabilize the bur and locate the unseen opening while contouring the bone. While a pair of wings are shown, it will be appreciated that a rhinoplasty bur according to the present invention can be formed with only one wing. The bur can also be formed without lip 28 but with wings 38.

As noted, the irrigation tube 30 extends along the exterior of outer tube 24 from coupling 32 to a closed distal end 34 with a pair of apertures (not shown) formed on a side of the tube 30 in communication with pocket 25 via a pair of inlets 42 in the outer tube adjacent the cutting tip to deliver irrigating fluid to the cutting tip.

When attached to a powered handpiece, such as the Xomed STRAIGHTSHOT® handpiece, the rhinoplasty bur 10 according to the present invention offers rhinoplasty surgeons the ability to sculpt the bony dorsum with a high degree of finesse and control, allows surgeons to achieve a more reproducible dorsal hump removal when compared with manual osteotomes and is particularly useful in revision cases, where spot burring is often necessary to correct localized irregularities. The bur 10 can be used wherever a rasp would be applicable, with less soft tissue trauma.

The rhinoplasty bur according to the present invention is ideal for use in external rhinoplasties where the surgical site can be directly visualized and is especially effective in patients with thin nasal skin where even the slightest bony irregularity can result in a visible or palpable deformity. The rhinoplasty bur according to the present invention can also be used to safely modify the nasal radix.

The configuration of the distal end of the outer tubular member, i.e. pocket 25 combined with the position of opening 26 with lip 28 and/or wings 38, provides both distal protection and extreme radial protection projecting beyond the cutting area. The wings 38 provide shielding or spacing of tissue while burring dorsal bone during either open or closed rhinoplasty procedures and also provide a means for the surgeon to stabilize the bur and locate the unseen opening while contouring the bone. A suction passage for aspiration of cut tissue or debris is formed through the outer tubular member in a straight path and aspiration is assisted by the irrigating fluid supplied to pocket 25 and, thus, to bur 20 which prevents clogging. The suction passage can extend through inner member 18 via suction inlet 40 and can extend around inner member 18.

Inasmuch as the present invention is subject to many variations, modifications, and changes in detail, it is intended that all subject matter discussed above or shown in the accompanying drawings be interpreted as illustrative only and not be taken in a limiting sense.

What is claimed is:

1. A rhinoplasty bur for use with a powered handpiece comprising
    an outer tubular member including a distal end forming a pocket having a bottom wall, an opposed upper opening and a curved end wall forming a protective lip extending upwardly from said bottom wall, said distal end of said outer tubular member including at least one inlet opening in said bottom wall aligned with said upper opening and communicating with said pocket;
    an inner bur assembly rotatably received in said outer tubular member and having a proximal end for mounting to a powered handpiece and a distal end formed of a bur received in said pocket and protected distally by said lip;
    an irrigation tube extending exteriorly alongside said outer tubular member and communicating with said at least one inlet opening to provide irrigation fluid to said pocket; and
    a suction passage extending through said outer tubular member for aspiration of irrigation fluid and cut tissue.

2. A rhinoplasty bur for use with a powered handpiece comprising
    an outer tubular member including a distal end forming a pocket having a bottom wall, an opposed upper opening and a curved end wall forming a protective lip extending upwardly from said bottom wall, said distal end of said outer tubular member including a curved wing extending laterally outwardly from a side of said pocket;
    an inner bur assembly rotatably received in said outer tubular member and having a proximal end for mounting to a powered handpiece and a distal end formed of a bur received in said pocket and protected distally by said lip; and
    a suction passage extending through said outer tubular member for aspiration of cut tissue.

3. A rhinoplasty bur for use with a powered handpiece comprising
    an outer tubular member including a distal end forming a pocket having a bottom wall, an opposed upper opening and a curved end wall forming a protective lip extending upwardly from said bottom wall, said distal end of said outer tubular member including a pair of opposed curved wings extending laterally outwardly from opposing sides of said pocket;
    an inner bur assembly rotatably received in said outer tubular member and having a proximal end for mounting to a powered handpiece and a distal end formed of a bur received in said pocket and protected distally by said lip; and
    a suction passage extending through said outer tubular member for aspiration of cut tissue.

4. A rhinoplasty bur for use with a powered handpiece as recited in claim 3 and further comprising an irrigation tube extending along said outer tubular member and communicating with said pocket to provide irrigating fluid thereto.

5. A rhinoplasty bur for use with a powered handpiece comprising
    an outer tubular member including a distal end forming a pocket having a bottom wall, an opposed upper opening with a pair of opposed longitudinal edges and a curved wing extending laterally outwardly from each of said longitudinal edges;
    an inner bur assembly rotatably received in said outer tubular member and having a proximal end for mounting to a powered handpiece and a distal end formed of a bur received in said pocket between said curved wings; and
    a suction passage extending through said outer tubular member fore aspiration of cut tissue.

6. A rhinoplasty bur for use with a powered handpiece as recited in claim 5 and further comprising an irrigation tube extending along said outer tubular member and communicating with said pocket to provide irrigating fluid thereto.

* * * * *